US007964397B2

(12) United States Patent
Rathe et al.

(10) Patent No.: US 7,964,397 B2
(45) Date of Patent: *Jun. 21, 2011

(54) METHOD FOR THE CULTIVATION OF PRIMARY CELLS AND FOR THE AMPLIFICATION OF VIRUSES UNDER SERUM FREE CONDITIONS

(75) Inventors: Ingmar Rathe, Olching (DE); Eva Felder, Munich (DE); Karl Heller, Unterfohring (DE)

(73) Assignee: Bavarian Nordic A/S, Kvistgaard (DK)

( * ) Notice: Subject to any disclaimer, the term of this patent is extended or adjusted under 35 U.S.C. 154(b) by 80 days.

This patent is subject to a terminal disclaimer.

(21) Appl. No.: 12/243,332

(22) Filed: Oct. 1, 2008

(65) Prior Publication Data
US 2009/0029459 A1  Jan. 29, 2009

Related U.S. Application Data

(63) Continuation of application No. 11/071,814, filed on Mar. 3, 2005, now Pat. No. 7,695,939, which is a continuation of application No. PCT/EP03/09704, filed on Sep. 1, 2003.

(30) Foreign Application Priority Data

Sep. 5, 2002 (DK) .................................. 2002 1302

(51) Int. Cl.
*A01N 63/00* (2006.01)
*A61K 39/00* (2006.01)
*A61K 39/275* (2006.01)
*A61K 45/00* (2006.01)
*C12N 5/07* (2010.01)
*C12N 7/00* (2010.01)
*C12N 7/02* (2010.01)
*C12N 5/00* (2010.01)
*C12P 1/00* (2006.01)
*C12P 21/04* (2006.01)
*A61K 39/165* (2006.01)

(52) U.S. Cl. ... 435/349; 424/93.6; 424/93.7; 424/184.1; 424/232.1; 424/281.1; 435/41; 435/70.1; 435/235.1; 435/239; 435/384

(58) Field of Classification Search .................. None
See application file for complete search history.

(56) References Cited

U.S. PATENT DOCUMENTS

| 3,887,430 A | 6/1975 | Torney et al. |
| 4,072,565 A | 2/1978 | Weiss et al. |
| 5,024,947 A | 6/1991 | Inlow et al. |
| 5,155,020 A | 10/1992 | Paoletti |
| 5,185,146 A | 2/1993 | Altenburger et al. |
| 5,403,582 A | 4/1995 | Nazerian et al. |
| 5,405,772 A | 4/1995 | Ponting |
| 5,494,807 A | 2/1996 | Paoletti et al. |
| 5,550,051 A | 8/1996 | Mundt et al. |
| 5,753,489 A | 5/1998 | Kistner et al. |
| 5,756,341 A | 5/1998 | Kistner et al. |
| 5,789,245 A | 8/1998 | Dubensky et al. |
| 6,100,061 A | 8/2000 | Reiter et al. |
| 6,146,873 A | 11/2000 | Kistner et al. |
| 6,761,893 B2 | 7/2004 | Chaplin et al. |
| 6,913,752 B2 | 7/2005 | Chaplin et al. |
| 6,924,137 B2 | 8/2005 | Howley et al. |
| 7,056,723 B2 | 6/2006 | Heller et al. |
| 7,097,842 B2 | 8/2006 | Suter et al. |
| 7,189,536 B2 | 3/2007 | Chaplin et al. |
| 7,335,364 B2 | 2/2008 | Chaplin et al. |
| 7,384,644 B2 | 6/2008 | Chaplin et al. |
| 7,445,924 B2 | 11/2008 | Chaplin et al. |
| 7,695,939 B2 | 4/2010 | Rathe et al. |
| 2002/0022268 A1 | 2/2002 | Xu et al. |
| 2003/0013190 A1 | 1/2003 | Mayr |
| 2003/0228330 A1 | 12/2003 | Falkner et al. |
| 2004/0058441 A1 | 3/2004 | Pain et al. |
| 2004/0234950 A1 | 11/2004 | Howley et al. |
| 2005/0214323 A1 | 9/2005 | Chaplin et al. |
| 2005/0214324 A1 | 9/2005 | Rathe et al. |
| 2006/0093620 A1 | 5/2006 | Falkner et al. |
| 2006/0127984 A1 | 6/2006 | Ackermann et al. |

(Continued)

FOREIGN PATENT DOCUMENTS
EP  0584788 A2  3/1994
(Continued)

OTHER PUBLICATIONS

Balk et al., Epidermal growth factor and insulin cause normal chicken heart mesenchymal cells to proliferate like their Rous sarcoma virus-infected counterparts, Proc. Nat. Acad. Sci. USA 79: 1154-1157 (1982).

Couchman et al.,Fibronectin Has a Dual Role in Locomotion and Anchorage of Primary Chick Fibroblasts and Can Promote Entry into the Division Cycle, J. Cell. Biol. 93: 402-410 (1982).

Kwon et al., Test on Growth and Maintenance Examination of Chick Embryo Fibroblast in the Medium to Which Chicken Embryo Amnio-Allantoic Fluid is Added Instead of Bovine Serum, Agriculture Test Research Report No. 20 (Livestock Hygiene Sericulture Section): 5-9 (1978).

(Continued)

*Primary Examiner* — Zachariah Lucas
*Assistant Examiner* — Benjamin P Blumel
(74) *Attorney, Agent, or Firm* — Law Office of Salvatore Arrigo and Scott Lee, LLP

(57) ABSTRACT

The present invention relates to a method for the cultivation of primary cells. The primary cells are cultivated in a serum free medium comprising a factor selected from the group consisting of growth factors and attachment factors. The method for the cultivation of primary cells may be one step in a method for the amplification of viruses, such as poxviruses. According to this latter method the primary cells are cultivated in a serum free medium comprising a factor selected from the group consisting of growth factors and attachment factors. The cells are then infected with the virus and the infected cells are cultivated in serum free medium until progeny virus is produced.

20 Claims, No Drawings

U.S. PATENT DOCUMENTS

| | | | |
|---|---|---|---|
| 2006/0280758 | A1 | 12/2006 | Chaplin et al. |
| 2008/0089907 | A1 | 4/2008 | Chaplin et al. |
| 2010/0111999 | A1 | 5/2010 | Guehenneux et al. |

FOREIGN PATENT DOCUMENTS

| | | | |
|---|---|---|---|
| JP | H9-154571 | A1 | 6/1997 |
| WO | WO 92/05246 | A1 | 4/1992 |
| WO | 95/22978 | A1 | 8/1995 |
| WO | WO96/15231 | A1 | 5/1996 |
| WO | WO 97/02355 | A1 | 1/1997 |
| WO | WO 97/31119 | A1 | 8/1997 |
| WO | WO98/04680 | A1 | 2/1998 |
| WO | WO 98/04680 | A1 | 2/1998 |
| WO | WO 98/15614 | A1 | 4/1998 |
| WO | WO98/15614 | A1 | 4/1998 |
| WO | WO 98/56919 | A1 | 12/1998 |
| WO | WO 99/07869 | A1 | 2/1999 |
| WO | WO 00/28016 | A1 | 5/2000 |
| WO | WO 00/29428 | A1 | 5/2000 |
| WO | WO 01/68820 | A1 | 9/2001 |
| WO | WO 01/89559 | A1 | 11/2001 |
| WO | WO 02/24224 | A1 | 3/2002 |
| WO | WO02/24876 | A2 | 3/2002 |
| WO | WO 02/42480 | A1 | 5/2002 |
| WO | WO03/008533 | A2 | 1/2003 |
| WO | 03/054175 | A1 | 7/2003 |
| WO | WO03/054174 | A1 | 7/2003 |

OTHER PUBLICATIONS

Nakamura et al., Tyrosine Phosphorylation of Specific Proteins After Mitogen Stimulation of Chicken Embryo Fibroblasts, Mol. Cell Biol. 3:380-390 (1983).

Pietrzkowski et al., Cellular Activities Associated with the Transition of Chick Embryo Fibroblasts from Stationary to Proliferation State, Folia Histochemica et Cytobiologica vol. 27:183-196 (1969).

Price et al., Serum-Free Medium Without Animal Components for Virus Production, FOCUS vol. 19 No. 3, 67-69 (1997).

Zell- Und Gewebekultur, Einführung in die Grundiagen sowie ausgewählte Methoden und Anwendungen, Lindl et al., Gustav Fischer Verlag, Stuttgart, New York, p. 57 (1987).

Life Technologies, Product description of VP-SFM (May 1999).

Focus on Alternatives, Serum Free Media for Cell Culture (Aug. 2006).

Grob et al., Role of the Individual Interferon Systems and Specific Immunity in Mice in Controlling Systemic Dissemination of Attenuated Pseudorabies Virus Infection, 1999, Journal of Virology, vol. 73, No. 6, pp. 4748-4754.

Carroll, MW, and Moss, B. 1997, Virology 238:198-211.

Meyer, H, et al. Mapping of deletions in the genome of the highly attenuated vaccinia virus MVA and their influence on virulence. J. Gen. Virol. 1991, 72:1031-1038.

Marhoul, Z, et al. Cultivation of Lednice (Yaba1) virus in goose, duck and chick embryo cells. 1976, Acta Virol. 20:499-505. (Abstract).

Ivanov, I, et al. Propagation of avian pox virus vaccine strains in duck embryo cell line—Dec. 99, 2001, Experimental Pathology and Parasitology 4/6, pp. 46-49.

Asher D.M., Bovine Sera Used in the Manufacture of Biologicals: Current Concerns and Policies of the U.S. Food and Drug Administration Regarding the Transmissible Spongiform Encephalopathies, 1999, Developments in Biological Standardization, vol. 99, pp. 41-44.

Kozak et al., Transmissible Spongiform Encephalopathies (TSE): Minimizing the Risk of Transmission of Biological/ Biopharmaceutical Products: an Industry Perspective, 1996, Developments in Biological Standardization, vol. 88, pp. 257-264.

Pietrzkowski, et al. "Dextran 1-500 improves survival and spreading of chick embryo cells in serum-free medium" Folia Histochemica et Cytobiologica, vol. 26 No. 3, 1988, p. 123-132.

Stittelaar, et al., Vaccine 19: 3700-3709, 2001.

Sutter and Moss, Proc. Natl. Acad. Sci. USA 89:10847-51, 1992.

Schiefiinger, et al., Proc. Natl. Acad. Sci. USA 89:9977-81, 1992.

Merchlinsky, et al., Virology 190:522-6, 1992.

Moss, et al. "Host range restricted, non-replicating vaccinia vires vectors as vaccine candidates." Advances in Experimentaly Medicine and Biology, 397:7-13, 1996.

Wyatt, et al., PNAS 101:4590-4595, 2004.

Earl, et al., Nature 428: 182-185, 2004.

A. Mayr, ZBL Vet B 23, 417-430 (1976).

Blanchard, JT, et al., Journal of General Virology, 79, 1159-1167, 1998.

Bender, et al. Journal of Virology, vol. 70, No. 9, pp. 6418-6424, 1996.

Schneider, et al. Nature Medicine, 4, 397-402, 1998.

Sutter, et al. Vaccine 12, 1032-1040, 1994.

Eo, et al., The Journal of Immunology 166: 54735479, 2001.

Holzer, et al., Journal of Virology 73: 4536-4542, 1998.

Antoine, et al., Virology 244: 365-396, 1998.

Gilbert, et al., Biol. Chem. 380: 299-303, 1999.

Behera, et al., Hum. Gene Ther. 13 (14): 1697-709, 2002.

Belyakov, et al., Proc. Natl. Acad. Sci. 100: 9458-9463, 2003.

Hanke, et al., Journal of Virology 73: 7524-7532, 1999.

Bitterman et al., Role of fibronectin as a growth factor for fibroblasts, Journal of Cell Biology 97:1925-1932, 1983.

Clark et al., Serum supplements and serum-free media: applicability for microcarrier culture of animal cells, Developments in Biological Standardization 50:81-91, 1981.

Iding et al., An automatic system for the assessment of complex medium additives under cultivation conditions, Biotechnology and Bioengineering 73:442-448, 2001.

Vettese-Dadey M, One to Grow on, The Scientist 13:20, 1999.

Hundt et al., Serum free cultivation of primary embryo fibroblasts in microcarrier systems for vaccine production, Animal Cell Technology Meets Genomics, 771-774, 2005.

Gilbert et al, Current status for high titre poxvirus stock preparation in CEF under serum-free conditions: implications for vaccine development, Cytotechnology 28:79-88, 2005.

Geistlich and Gehring, Isolation and characterization of a novel type of growth factor derived from serum-free conditioned medium of chicken embryo fibroblasts, European Journal of Biochemistry 207: 147-153, 1992.

Gospodarowicz et al., Growth Factors in Mammalian Cell Culture, Annu. Rev. Biochem. 45, 531-558 (1976).

McMurtry et al., Developmental Changes in Embryonic and Extra-Embryonic Insulin-Like Growth Factor-I Tissue Concentrations in the Turkey Embryo, Poultry Science 76, 894-900 (1997).

Karcher et al., Developmental changes in amniotic and allantoic fluid insulin-like growth factor (IGF)-I and -II concentrations of avian embryos, Comparative Biochemistry and Physiology, Part A 142, 404-409 (2005).

Flamme et al., Mitogenic activity of chicken chorioallantoic fluid is temporally correlated to vascular growth in the chorioallantoic membrane and related to fibroblast growth factors, Development 111, 683-690 (1991).

Geistlich et al., CDGF (Chicken Embryo Fibroblast-Derived Growth Factor) Is Mitogenically Related to TGF-B and Modulates PDGF, bFGF, and IGF-1 Action on Sparse NIH/3T3 Cells, Exp. Cell Res. 204, 329-335 (1993).

Smith et al., Identification of a novel growth factor with transforming activity secreted by individual chick embryos, Development 109, 905-910 (1990).

Glover et al., Interaction of Phenol Red with Estrogenic and Antiestrogenic Action on Growth of Human Breast Cancer Cells ZR-75-1 and T-47-D, Cancer Res. 48, 3693-3697 (1988).

Invitrogen, Technical Resources—Media Formulation of RPMI Medium 1640, Dec. 13, 2010.

Invitrogen, Technical Resources—Media Formulation of MEM liquid, Dec. 13, 2010.

Wikipedia, Growth Factors, Dec. 13, 2010.

Sigma-Aldrich, Attachment Factors, Dec. 13, 2010.

Bavarian Nordic, Response to Oppositions, Opposition EP 11434858, Sep. 8, 2009.

Bavarian Nordic, Response to Preliminary Opinion, Opposition EP 11434858, Dec. 22, 2010.

European Patent Office, Summons and Preliminary Opinion, Opposition EP 11434858, May 18, 2010.

Grund, Response to Preliminary Opinion, Opposition EP 11434858, Dec. 22, 2010.

Cabinet Regimbeau, Response to Preliminary Opinion, Opposition EP 11434858, Dec. 22, 2010 (English Translation).

Cabinet Regimbeau, Opposition, Opposition EP 11434858, Jan. 26, 2009 (English Translation).

Grund, Opposition, Opposition EP 11434858, Jan. 23, 2009.

Baxter Aktiengesellschaft, Opposition, Opposition EP 11434858, Jan. 23, 2009.

Oxford Biomedica, Opposition, Opposition EP 11434858, Jan. 23, 2009.

Sanofi Pasteur, Opposition, Opposition EP 11434858, Jan. 23, 2009.

EP Patent No. 1434858, Amended Patent Claims from Oral Proceeding, Opposition to EP Patent No. 1434858, Jan. 27, 2011.

Dollenmeier et al., Proliferation and Differentiation of Chick Skeletal Muscle Cells Cultured in a Chemically Defined Medium, Exp. Cell. Res. 135:47-61 (1981).

Biochrom, AG, BMS Serum Alternative, Cat. No. S 5173. Siete 1, von 2.

METHOD FOR THE CULTIVATION OF PRIMARY CELLS AND FOR THE AMPLIFICATION OF VIRUSES UNDER SERUM FREE CONDITIONS

This application is a continuation of U.S. application No. Ser. 11/071,814, filed Mar. 3, 2005, which is a continuation of International Application PCT/EP03/009704, filed Sep. 1, 2003, which claims the benefit of PA 2002 01302, filed Sep. 5, 2002. All of these applications are incorporated by reference herein.

FIELD OF THE INVENTION

The present invention provides a method for the cultivation of primary cells. The primary cells are cultivated in a serum free medium comprising a factor selected from the group consisting of growth factors and attachment factors. The method for the cultivation of primary cells may be one step in a method for the amplification of viruses, wherein the cells are then infected with a subject virus and the infected cells are cultivated in serum free medium until progeny virus is produced. The invention encompasses the cultivation of poxviruses according to this method.

BACKGROUND OF THE INVENTION

Most viral vaccines such as attenuated or recombinant viruses are manufactured from cell culture systems. The cells used for virus/vaccine production may be cell lines, i.e. cells that grow continuously in vitro, either as single-cell suspension culture in bioreactors or as a monolayer on a cell-support surface of tissue culture flasks or roller-bottles. Some examples for cell lines used for the production of viruses are: the human fetal lung cell-line MRC-5 used for the manufacture of polio viruses and the human fetal lung cell-line WI-38 used for the manufacture of measles virus, mumps virus and rubella virus (MMR II) (Merck Sharp & Dohme).

Not only cell lines but also primary animal cells are used for the manufacture of vaccines. An example of primary cells that are used for virus production are chicken embryo fibroblasts (CEF cells). These cells are used for the production of measles and Japanese encephalitis virus (Pasteur Merieux), mumps virus (manufactured by Provaccine), rabies virus (manufactured by Chiron Berhing GmbH & Co.), yellow fever virus (manufacture by Aprilvax), influenza virus (manufactured by Wyeth Labs and SmithKline & Beecham) and modified Vaccinia virus Ankara (MVA).

CEF cells are often used since many virus vaccines are made by attenuating the virulent disease-causing virus by serially passaging in CEF cells. The attenuated virus does not longer cause the disease but is still capable of stimulating a potent protective immunity against the virulent form of the virus. An example for this type of virus is MVA. This virus is severely replication restricted in humans and in most animals. MVA is being developed as a vaccine vector because it can be used to express antigens derived from a variety of agents causing diseases in humans. Attenuated viruses, such as MVA are preferably not propagated on human cells since there is a concern that the viruses might become replication competent in cells of human origin. Viruses that have regained the ability to replicate in human cells represent a health risk if administered to humans, in particular if the individuals are immune compromised. For this reason, some attenuated viruses, such as MVA, are strictly manufactured from CEF cells, if intended for human use.

Moreover, CEF cells are used for those viruses that grow only on said cells. Examples of such viruses are avian viruses such as avipox viruses, canary pox virus, ALVAC, Fowl pox virus and NYVAC.

Cell lines and primary cells grown under in vitro culturing conditions require a special growth and maintenance medium that can support (I) cell replication in the logarithmic phase and (II) cell maintenance once the cells are no longer dividing, i.e., when the cells are in the stationary phase. The commonly used cell culture media comprise a rich salt solution containing vitamins, amino acids, essential trace elements and sugars. Growth hormones, enzymes and biologically active proteins required for supporting cell growth and maintenance are usually added as a supplement to the medium in the form of an animal blood derived serum product. Examples of animal blood derived serum products are fetal calf serum, chicken serum, horse serum and porcine serum. These sera are derived from fractionated blood, from which the red blood cells and the white blood cells have been removed. Primary cells, such as CEF cells are even more dependant on animal serum sources than cell lines. Thus, primary cells are usually cultivated in cell culture media comprising 5 to 10% serum, in most cases fetal calf serum (FCS).

The animal sera not only comprise factors that are required for the growth of cells, but also factors that are required for cells that naturally grow as adherent cells to attach to the cell support surface of the culture vessel. Thus, it is critical for adherent cells that enough serum is added to the medium to enable them to grow and form a monolayer.

Unfortunately, bovine/fetal calf serum as well as sera from other animals may contain adventitious pathogenic agents such as viruses or prion proteins. There is a potential risk that these pathogenic agents may be transmitted to the animal/human to be treated or vaccinated with the vaccine or any other pharmaceutical product produced in cell culture. This is of particular relevance if cell culture products are administered to immune-compromised humans. One of the many potential major problems associated with the commonly used bovine serum supplement is the possibility to transmit the agent causing bovine spongiforme encephalopathy (BSE) to the animals/humans that come into contact with the products produced from cell culture.

In view of the possible risk associated with the use of animal sera in cell culture it has become clear that manufacturing processes free from the use of animal products are highly desirable.

To this end, specific media that do not have to be supplemented with animal sera have been developed for continuously growing cell lines and for the production of viruses in continuously growing cell lines, respectively. An example of such a serum free medium that can be used to cultivate cell lines is VP-SFM manufactured by Gibco BRL/Life Technologies. According to the manufacturer's information VP-SFM is designed specifically for the growth of VERO, COS-7, MDCK, Hep2, BHK-21 and other important cell lines (Price, P. and Evege, E. Focus 1997, 19: 67-69) and for virus production in said cell lines. No information is available regarding the cultivation of primary cells in the medium.

THE PRESENT INVENTION

Summary of the Invention

What we therefore believe to be comprised by our invention may be summarized inter alia in the following words:
A method for the amplification of a virus comprising:
cultivating primary avian cells permissive for productive replication of the virus in a serum free medium comprising a factor selected from the group consisting of growth factors and attachment factors,
infecting of the primary avian cells with the virus,
cultivating the infected cells in serum free medium until progeny virus is produced, and
isolating the virus from the culture; such a
method, wherein the serum free medium comprising growth factors and attachment factors is removed at the time of infecting the primary avian cells with the virus, and/or during cultivating of the infected cells until virus progeny is produced, and replaced with a serum free medium which does not comprise growth factors and attachment factors; such a
method wherein, subsequent to cultivating the infected cells in serum free medium until progeny virus is produced, one or more virus purification steps are performed; such a
method wherein the virus used for infection of primary avian cells was previously propagated or may have been previously propagated in the presence of animal sera and is subsequently re-derived through several rounds of plaque purification by limited dilution in serum free medium to reduce the risk of serum contamination; such a
method which is repeated at least once to obtain a virus or virus stock which is essentially free of products and/or infectious agents comprised in animal sera; such a
method wherein the primary avian cells are Chicken Embryo Fibroblasts (CEF); such a
method wherein the growth factor is an epidermal growth factor (EGF); such a
method wherein the epidermal growth factor (EGF), is recombinant-human EGF; such a
method wherein the concentration of EGF is in a range of 5 to 20 ng/ml medium; such a
method wherein the attachment factor is fibronectin; such a
method wherein the concentration of fibronectin is in the range of 1 to 10 ug/cm² surface of the cell culture vessel; such a
method wherein the medium comprises two or more factors selected from growth factors and attachment factors; such a
method wherein the medium comprises EGF and fibronectin in concentration ranges of 5 to 20 ng/ml and 1 to 10 ug/ml medium, respectively; such a
method wherein the medium further comprises one or more additives selected from a microbial extract, a plant extract and an extract from a non-mammalian animal; such a
method wherein the microbial extract is a yeast extract or a yeastolate ultrafiltrate; such a
method wherein the plant extract is a rice extract or a soya extract; such a
method wherein the extract from a non-mammalian animal is a fish extract; such a
method wherein the virus is selected from mumps virus, measles virus, rabies virus, Japanese encephalitis virus, yellow fever virus, influenza virus and poxvirus; such a
method wherein the poxvirus is an attenuated virus or a recombinant virus; such a
method wherein the poxvirus is an orthopoxvirus; such a
method wherein the orthopoxvirus is a Vaccinia virus; such a
method wherein the Vaccinia virus is Modified Vaccinia virus Ankara; such a method wherein the Modified Vaccinia virus Ankara is selected from MVA-575 (ECACC V00120707), MVA-572 (ECACC V94012707), and MVA-BN (ECACC V00083008), or a derivative of such virus; such a
poxvirus obtained by:
cultivating primary avian cells permissive for productive replication of the virus in a serum free medium comprising a factor selected from the group consisting of growth factors and attachment factors,
infecting the primary avian cells with the virus,
cultivating the infected cells in serum free medium until progeny virus is produced, and
isolating the virus from the culture; such a
poxvirus wherein the primary avian cells are Chicken Embryo Fibroblasts (CEF); such a
poxvirus wherein the virus used for infection of primary avian cells was previously propagated or may have been previously propagated in the presence of animal sera and which virus is subsequently re-derived through several rounds of plaque purification by limited dilution in serum free medium; such a
poxvirus wherein 4-6 rounds of plaque purification are performed; such a
poxvirus wherein the risk of the poxvirus to contain a BSE particle is less than $10^{32}$; such a
poxvirus which is essentially free of any products and/or infectious agents comprised in animal sera; such a
poxvirus wherein the poxvirus is Modified Vaccinia virus Ankara; such a poxvirus wherein the Modified Vaccinia virus Ankara is selected from MVA-575 (ECACC V00120707), MVA-572 (ECACC V94012707), and MVA-BN (ECACC V00083008), or a derivative of such virus; such a
poxvirus wherein the poxvirus is an attenuated virus or a recombinant virus; such a
vaccine comprising the poxvirus; such a
pharmaceutical composition comprising the poxvirus and a pharmaceutically acceptable carrier, diluent and/or additive; such a
pharmaceutical composition which is essentially free of any products and/or infectious agents comprised in animal sera; such a
method for the treatment of an animal, including a human, in need thereof, comprising administering to the animal, including a human, the poxvirus; such a
method wherein the poxvirus is administered as a vaccine; such a
method for the treatment of an animal, including a human, in need thereof, comprising administering to the animal, including a human, the pharmaceutical composition; such a
method for the vaccination of an animal, including a human, comprising administering to the animal, including a human, the vaccine; such a
method for enhancing a specific immune response to a vaccine in a living mammal, including a human, comprising administering a vaccine and an adjuvant-effective amount of the poxvirus.

DETAILED DESCRIPTION OF THE INVENTION

The present invention provides a method for cultivation of primary cells, in particular primary avian cells, in serum free medium and a method for the production of virus in primary cells under serum free conditions. The instant method for the cultivation of primary cells may be characterized in that the cells are cultivated in a serum free medium comprising a factor selected from the group consisting of growth factors and attachment factors.

According to the present invention primary cells that naturally grow as adherent cells attach to the surface of the cell culture vessel after seeding and grow in a logarithmic phase until a monolayer is formed. According to the present invention the resting cells may be maintained in the medium used during the attachment and logarithmic growth of the cells.

The term "primary cells" as used in the present description is well known to a person skilled in the art. Without being restricted to the following definition the term "primary cells" may refer to cells that have been freshly isolated from an animal or human tissue, organ or organism, wherein the cells are not able to continuously and indefinitely replicate and divide. Usually, primary cells divide in cell culture less than 100 times, often less than 50 times, often less than 25 times. Thus, primary cells have not undergone an immortalizing event. Examples for primary cells are cord blood lymphocytes and human or animal fibroblasts. Representative examples of animal fibroblasts are avian fibroblasts, such as Chicken Embryo Fibroblasts (CEF cells). An example of primary human fibroblasts is human foreskin fibroblasts.

Methods of isolating primary cells are known. Generally, primary cell cultures are derived directly from tissues, organs or embryos. The tissues, organs or embryos are subjected to protease treatment to obtain single cells. The cells are then cultivated according to the method of the present invention under in vitro culture conditions.

More specifically, CEF cells are obtained from protease digested chicken embryos. CEF cells grow best as adherent cells attached to a solid cell support surface. The cells start replication and establish a monolayer. If CEF cells (after embryo digestion) are cultivated in vitro with a standard culturing medium and without animal serum, the cells will occasionally attach to the solid cell-support surface, but will not replicate to form a confluent monolayer of cells and will, with time, slowly detach from the solid culturing-support surface. In contrast, if the CEF cells are cultivated according to the method of the present invention, the cells attach to the solid support, grow in the logarithmic phase until a monolayer is formed and can be maintained in the stationary phase for several days.

The method of the present invention is not restricted to cells that form monolayers. According to an alternative embodiment the method according to the present invention may be used for all other types of primary cells, such as cells naturally growing in suspension culture (e.g. lymphocytes or other types of blood cells) or cells that naturally would grow as adherent cells but have been adapted to growing in suspension culture.

As shown below the cells can also be used for the serum free amplification of viruses that might be useful as vaccines.

Viruses, including e.g. wild-type viruses, attenuated viruses and recombinant viruses that are used as vaccines, may be amplified under serum containing conditions. However as noted above, there is a potential risk that serum contains pathogenic agents (such as TSE/BSE) may be transmitted to the animal/human treated or vaccinated with the vaccine. To reduce the risk of contaminants in the vaccine, it is a further aspect of the invention to passage and/or cultivate and/or plaque purify and/or purify by limited dilution or any other method under serum free conditions those viruses that previously have been amplified or may have been previously amplified under serum containing conditions and that have been used or are intended to be used as vaccine. A virus that may by used in a vaccine and that is passaged and/or cultivated and/or plaque purified and/or purified by limited dilution or any other method under serum free conditions may be a wild-type virus, an attenuated virus or a recombinant virus.

It was unexpected that primary cells naturally growing as adherent cells (I) can effectively attach to the surface of the cell culture vessel without forming unacceptable amounts of aggregates and (II) can be grown in the logarithmic phase in the absence of serum since it is generally believed that primary cells are dependant on a multitude of different factors and components comprised in serum. Moreover, it is believed that adherent cells form non-viable aggregates that do not attach to the surface of the cell culture vessel, when cultivated in serum free medium. Thus, it was unexpected that it is sufficient to add to a serum free medium a factor selected from the group consisting of growth factors and attachment factors in order to obtain attachment and growth of adherent primary cells. Moreover, it was also unexpected that primary cells cultivated in suspension culture can be grown with the media used in the method according to the present invention.

Furthermore, it was surprising that primary avian cells, such as the instant Chicken Embryo Fibroblasts (CEF), can be cultivated to attach to the surface of a cell culture vessel without forming unacceptable amounts of aggregates in a serum free medium comprising a factor selected from the group consisting of growth factors and attachment factors. Avian cells are otherwise understood to grow adversely in serum free medium not comprising growth factors or attachment factors, i.e., it was unexpected that the poor growth properties of primary avian cells could be improved significantly by adding a factor selected from growth factors and attachment factors to serum free medium.

The term "cultivation of cells" in a serum free medium in the context of adherent primary cells refers to the seeding of the cells into the culture vessel in a serum free medium, to the growing of the cells in a serum free medium in the logarithmic phase until a monolayer is formed and/or to the maintenance of the cells in serum free medium as soon as the monolayer is formed. The term "cultivation of cells" in a serum free medium also refers to a method in which all of the above mentioned steps are performed with serum free medium, so that no animal serum products are present during the whole cultivation process of the cells. Thus, in a more general meaning the term "cultivation of cells in a serum free medium" refers to the fact that all media leading to the formation of a monolayer are serum free media. The media used in all of the above steps may comprise a factor selected from growth factors and attachment factors. However, it might be sufficient to add such a factor only to the media used for the attachment of the cells and/or the growing of the cells under logarithmic conditions.

The term "cultivation of cells" in a serum free medium in the context of cells growing in suspension culture refers to the seeding of the cells into the culture vessel in a serum free medium, the growing of the cells in a serum free medium in the logarithmic phase and/or the maintenance of the cells in serum free medium as soon as the saturation density at which no further replication occurs is obtained. The term "cultivation of cells" in a serum free medium refers to a method in which all of the above mentioned steps are performed with serum free medium, so that no animal serum products are present during the whole cultivation of the cells. The media used in all of the above steps may preferably comprise a factor selected from the group of growth factors. However, it might be sufficient to add such a factor only to the media used for the seeding of the cells and/or the growing of the cells under logarithmic conditions. As explained below in more detail it might also be possible to cultivate cells that would normally grow as attached cells also as suspension culture cells if appropriate incubation conditions are chosen (e.g. by applying "wave" incubation). The method according to the present invention also applies for this type of incubation.

The term "serum-free" medium refers to any cell culture medium that does not contain sera from animal or human origin. Suitable cell culture media are known to the person skilled in the art. These media comprise salts, vitamins, buffers, energy sources, amino acids and other substances. An example of a medium suitable for the serum free cultivation of CEF cells is medium 199 (Morgan, Morton and Parker; Proc. Soc. Exp. Biol. Med. 1950, 73, 1; obtainable inter alia from LifeTechnologies).

The media used according to the method of the present invention, in particular the media used for adherent cells such as CEF cells, contain a factor selected from the group consisting of growth factors and attachment factors. An example of an attachment factor is fibronectin.

For cells that naturally grow as adherent cells, which, however, are nevertheless cultivated in suspension culture (which is possible e.g. for CEF cells), it is a further aspect of the invention to use a factor selected from growth factors. Examples of growth factors useful for this type of cultivation are recombinant bovine, mouse, chicken, human epidermal growth factor (EGF), particularly recombinant human EGF (rh-EGF) (Chemicon Int., catalog number: GF001).

For cells naturally growing in suspension culture the medium may comprise a factor selected from the group of growth factors including EGF. Growth factors for these types of cells are factors specific for non-adherent cells. Examples of these growth factors are interleukins, GM-CSF, G-CSF and others. The person skilled in the art may easily determine by routine experimentation, which type of factor is suitable for which type of cells.

If the factor added to the serum free medium is EGF, in particular rh-EGF, it is an aspect of the invention to add such growth factor to the medium at a concentration of 1 to 50 ng/ml. It is a further aspect to add such factor at a concentration of 5 to 20 ng/ml. However, the person skilled in the art will be aware of the fact that different cell types may require a somewhat different concentration of EGF in the medium for optimal results.

If the attachment factor added to the serum free medium is fibronectin: (e.g. Chemicon Int.; Human plasma fibronectin; catalog number FC010), it is an aspect of the invention to add such factor to the medium at a concentration of 1 to 50. It is a further aspect to add such factor at a concentration of 1 to 10 μg/cm$^2$ surface of the cell culture vessel. However, those skilled in the art understand that different cell types may require a somewhat different concentration of fibronectin in the medium for optimal results.

It is sufficient to add only one factor selected from growth factors and attachment factors to the medium, in particular if the cells are adherent cells. However, it is also possible to add two or more factors selected from growth factors and attachment factors to the medium. The medium may comprise EGF and fibronectin, possibly in the concentration ranges defined above, in particular if the primary cells are adherent cells such as CEF cells.

The medium may further comprise one or more additives selected from microbial extracts, plant extracts and extracts from non-mammalian animals. The microbial extract may be a yeast extract or yeastolate ultrafiltrate. The plant extract may be a rice extract or soya extract. The extract from non-mammalian animals may be a fish extract.

Asparagine may also be added to the commercially available serum free medium to which a factor selected from growth factors and attachment factors has been added. Asparagine may also be added to the medium that is used during the infection with virus (see below). Commercial serum free media usually comprise asparagine in a concentration range of 0.3 to 1.0 mM. It is an aspect of the invention to add asparagine to supplement the medium in the range of 0.5 to 1.5 mM. A 1 mM asparagine supplement may be adequate. The total concentration of asparagine in the medium is less than 2 mM, in the range of 0.8 to 1.8 mM. For example, the concentration of asparagine in the medium is 1.3 mM.

Moreover, glutamine may also be added to the medium. Glutamine may also be added to the medium that is used during the infection with virus (see below). Glutamine may also be added to supplement the medium at concentrations in the range of 1 to 5 mM. It is a further aspect of the invention to add glutamine at a concentration in the range of 2 to 4 mM. The indicated ranges also correspond to the total concentrations in the medium since most of the commercially available media do not contain glutamine.

Amplification of a virus may comprise the following steps: in the first step primary cells are cultivated according to the method described above, i.e. primary cells are cultivated in a serum free medium comprising a factor selected from the group consisting of growth factors and attachment factors, depending on the cell type. All conditions and definitions given in the description of the method for the cultivation of primary cells above also apply to the definition of the first step of the method for the amplification of virus according to this embodiment of the present invention. In a second step the primary cells are infected with the virus. In the third step the infected cells are incubated in serum free medium until progeny virus is produced. Finally, in a fourth step, the virus is isolated from infected cells.

The term "amplification of a virus" is used to make clear that the method according to the present invention is typically used to increase the amount of virus due to a productive viral replication of the virus in the infected cells. In other words the ratio of output virus to input virus should be above 1. Primary cells are chosen for a specific virus in which the virus is able to productively replicate. The term "reproductive replication" refers to the fact that the specific virus replicates in the specific primary cell to such an extent that infectious progeny virus is produced, wherein the ratio of output virus to input virus is above 1.

The selection of primary cell type which supports productive replication of a particular virus is known. By way of example the primary cells may be human foreskin fibroblasts if the virus to be amplified is the human Cytomegalovirus; the primary cells may be CEF cells if the virus to be amplified is measles virus, mumps virus, rabies virus, Japanese encephalitis virus, yellow fever virus, influenza virus or a poxvirus such as vaccinia virus.

Methods for infecting primary cells according to the second step of instant method for virus amplification are known. By way of example the virus may simply be added to the medium. Alternatively, the medium may be removed and the virus may be added to fresh medium, which in turn is added to the cells. To obtain an efficient infection the amount of the virus/medium suspension should be as low as possible to have a high virus concentration. After the attachment of the virus additional medium may be added.

In the third step of the instant method, the infected cells are cultivated in serum free medium until progeny virus is produced.

The serum free medium that is used in the second and third step of the method for the amplification of a virus may be the same medium that has already been used before, i.e. a serum free medium comprising a factor selected from growth factors and attachment factors, depending on the cell type. Alternatively, the serum free medium comprising growth factors and attachment factors may be removed at the step of infecting the primary avian cells with the virus, and/or at the step of cultivating the infected cells until virus progeny is produced, and replaced with a serum free medium which is essentially free of growth factors and attachment factors without adverse effects on the culture.

During all stages the medium may be supplemented with asparagine and/or glutamine as outlined above, wherein the total concentration of asparagine in the medium is as defined above.

The progeny virus may be concentrated and purified according to methods known to the person skilled in the art.

Thus, the present invention relates to a method for the amplification of a poxvirus comprising the following steps: (I) cultivating primary cells according to a method as described above, i.e. a method in which the primary cells are cultivated in serum free medium comprising a factor selected from the group consisting of growth factors and attachment factors, depending on the cell type, (II) infecting the primary cells with the poxvirus, (III) cultivating the infected cells in serum free medium until progeny virus is produced and (iv) isolating the virus from the infected cells. Viruses isolated according to the instant method are free of any products and/or infectious agents comprised in animal sera.

The process of passaging and/or further cultivating and/or plaque purifying and/or purifying by limited dilution or any other method under serum free conditions those viruses that previously have been amplified under serum containing conditions is termed "re-derivation". Such a re-derivation may also be used if it is not completely clear how a master seed was obtained that is used for the production of a vaccine. A re-derivation under serum-free drastically reduces the risk of contaminations in the vaccine, in particular of undesired infectious agents.

The methods according to the present invention relate to cultivating primary avian cells and to amplifying a virus, wherein the virus is the virus that is to be re-derived. For example, the instant methods are useful for the re-derivation of viruses and virus stocks, in particular for stocks that have been, or may have been passaged in serum containing medium and/or with unclear passage histories.

One passage of the starting material, i.e. of the virus to be re-derived under serum free conditions, may be sufficient for the re-derivation of a virus. The term "passaging" refers to the steps of cultivating cells under serum free conditions, infection of the cells with the virus to be re-derived and obtaining the virus produced in the infected cells. Although one passage might be sufficient, it may be preferable to passage the virus several times under serum free conditions. In this case the virus obtained from the first passaging step is used to again infect fresh cells. The passaging under serum free conditions may be combined with one or more plaque purifications and/or with limited dilution and/or any other method for the purification of a virus under serum free conditions. The total number of passages, optionally by including plaque purification and/or limited dilution is in a range of 1 to more than 10, such as 3 to 8 or 4 to 6. The techniques of plaque purification and/or limited dilution are standard virological methods practiced by those skilled in the art.

The re-derivation according to the present invention may be done with a virus starting material that exhibits desired biological properties, wherein the virus used as starting material may have been amplified under serum containing conditions. After several passages under serum free conditions according to the present invention it is confirmed whether the virus passaged under serum free conditions is identical/similar to the virus originally passaged under serum containing methods. In most cases the virus obtained after the re-derivation has similar/identical properties to the virus used as starting material. There may also be situations in which the re-derived virus has even improved properties compared to the virus used as starting material, e.g. an improved safety profile.

The present invention also relates to the re-derived virus obtained by the method according to the present invention. The risk that poxvirus obtained by the re-derivation method according to the present invention comprises a BSE particle is less than $10^{32}$.

If it is intended to re-derive a virus, the following re-derivation plan may be used by way of example. This plan is particularly suitable for the re-derivation of a Vaccinia virus, e.g. an MVA strain that has or may have been cultivated under serum containing conditions: First the original Master Virus Bank (MVB) virus seed stock is re-cloned through, for example, 5 rounds of plaque purification by limited dilution (see example 9). Viruses from the original virus seed stock and from the new re-derived stock are compared both genetically and phenotypically. A genetic comparison of the virus cultivated under serum containing conditions and the re-derived virus may be made by, for example, (i) Restriction Enzyme mapping of the viral genome (RE-Map), (ii) PCR amplification of relevant parts of the genome such as the six deletion sites in case on MVA and/or (iii) PCR based restriction fragment length polymorphism mapping of the viral genome (PCR-RFLP Assay). A phenotypic characterization may, for example, be performed by: (i) comparing humoral responses in vaccinated mice, (ii) comparing efficacy using a lethal vaccinia model, (iii) evaluating safety by the vaccination of severely immune compromised mice, (iv) comparing the attenuation (replication) in a variety of mammalian cell lines.

The present invention consequently relates to a re-derivation process namely the method for the cultivation of primary avian cells as defined above and/or the method for the amplification of a virus as defined above, wherein the virus is the virus that is to be re-derived. The invention further relates to re-derived virus such as re-derived Vaccinia viruses, e.g. MVA strains such as MVA-BN. The re-derived virus can be e.g. a re-derived wild type virus, a re-derived attenuated virus or a re-derived recombinant virus. The invention further relates to compositions comprising re-derived virus.

The invention further relates to a virus including a re-derived virus, in particular to the viruses including the re-derived viruses as defined above as a medicament or vaccine. If the virus is a wild-type virus or an attenuated virus the virus can be used for vaccination against the virus as such. For this purpose attenuated viruses are particularly preferred. If the virus is a recombinant virus expressing proteins expressed from genes heterologous to the viral genome, it is possible to vaccinate against the virus as such and/or against the expressed heterologous protein. If the recombinant virus expresses a therapeutic gene such as an antisense RNA or a ribozyme the virus may be used as a medicament.

The term "recombinant virus" refers to any virus having inserted into the viral genome a heterologous gene that is not naturally part of the viral genome. A heterologous gene can be a therapeutic gene, a gene coding for a peptide comprising at least one epitope to induce an immune response, an antisense expression cassette or a ribozyme gene. Methods to construct recombinant viruses are known to a person skilled in the art. Poxvirus vectors such as MVA, in particular MVA 575, MVA 572, and MVA-BN may be used (see above).

An "attenuated virus" is a virus originating from a pathogenic virus but that upon infection of the host organism leads to a lower mortality and/or morbidity compared to the non-attenuated parent virus. Examples of attenuated poxviruses are known to the person skilled in the art. An example for an attenuated Vaccinia virus is strain MVA, in particular the strain that has been deposited at ECACC with the deposition number V00083008 (see above).

As discussed previously, it is understood by those skilled in the art that primary avian cells grow adversely under serum free conditions. The additional stress associated with a poxvirus infection may be expected to cause the already stressed cells to die before a significant amplification of the poxvirus occurs. Surprisingly, avian cells grown according to the present method, in a serum free medium comprising a factor selected from growth factors and attachment factors, effectively support viral replication and amplification of poxviruses.

The poxvirus is preferably an orthopoxvirus. Examples of orthopox viruses are avipoxviruses and vaccinia viruses.

The term "avipoxvirus" refers to any avipoxvirus, such as Fowlpoxvirus, Canarypoxvirus, Uncopoxyirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

An example of a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5 and TROVAC (U.S. Pat. No. 5,766,598). FP-1 is a Duvette strain modified to be used as a vaccine in one-day old chickens. The strain is a commercial fowlpox virus vaccine strain designated 0 DCEP 25/CEP67/2309 October 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

Examples of vaccinia virus strains are the strains Temple of Heaven, Copenhagen, Paris, Budapest, Dairen, Gam, MRIVP, Per, Tashkent, TBK, Tom, Bern, Patwadangar, BIEM, B-15, Lister, EM-63, New York City Board of Health, Elstree, Ikeda and WR. The invention is preferably carried out with modified vaccinia virus Ankara (MVA) (Sutter, G. et al. [1994], Vaccine 12: 1032-40). Typical MVA strains are MVA 575 that has been deposited at the European Collection of Animal Cell Cultures under the deposition number ECACC V00120707 and MVA-572 deposited at ECACC under the deposition number V94012707. MVA-BN has been deposited at the European Collection of Animal Cell Cultures with the deposition number ECACC V00083008.

The virus to be amplified according to the method of the present invention may be a wild-type virus, an attenuated virus or a recombinant virus.

As pointed out above, for poxviruses the primary cells may be primary avian cells such as CEF cells or primary duck embryo fibroblasts. Again, one skilled in the art understands which primary cells are suitable for the amplification of which poxvirus. CEF cells are known for the amplification of MVA. If the method according to the present invention is used for the amplification of MVA in CEF cells, the starting pH of the medium may be in a range of about 7.0 to about 8.5. For MVA amplification in CEF cells in serum free medium, it is an aspect of the invention to select one or two of the factors selected from EGF and fibronectin.

The invention further refers to viruses, in particular poxviruses obtained by the above-described method. According to a preferred embodiment the poxvirus is a vaccinia virus, most preferably a MVA strain such as MVA-BN.

The invention further concerns a composition comprising a virus, in particular a poxvirus produced by the method according to the present invention. As pointed out above the poxvirus is preferably a vaccinia virus, most preferably a MVA strain such as MVA-BN. Due to the method for amplification of the virus the composition is free of any products and/or infectious agents comprised in animal sera. In contrast, compositions comprising viruses produced according to conventional methods comprise residual compounds derived from animal serum. This is especially the case for compositions comprising poxviruses produced according to conventional methods, such as vaccinia virus strains.

The invention further relates to the use of a virus as defined above or a composition as defined above for the manufacture of a vaccine.

The invention further concerns a method for the treatment or vaccination of an animal, including a human, in need thereof, comprising the administration of a virus as defined above or a composition as defined above to the animal or human body.

EXPERIMENTAL PART

The present invention will be better understood in connection with the following examples, which are intended as an illustration of and not a limitation upon the scope of the invention.

Example 1

Preparation of Chicken Embryo Fibroblast (CEF) Cells

Specific pathogen free (SPF) fertilized eggs were stored not longer than 12 days at 4° C. The eggs were put into an incubator and incubated for 10-12 days at 37.8° C.±8° C. One petri dish per maximum 11 eggs was prepared with 10-20 ml PBS. The eggs were put in a dedicated egg carton and treated extensively with Bacillol® to sterilize the outside of the egg shell. After drying, a hole was made into the eggs and the shell was removed carefully. The chorioallantoic membrane was put aside. The embryos were lifted up by the feet and then their heads were cut off. The embryos were then transferred into the prepared petri dishes. After removing the feet the trunks were washed again with PBS. 11 trunks maximum were put into a 20 ml plastic syringe and squeezed into an Erlenmeyer flask. 5 ml of prewarmed (37° C.) Trypsin/EDTA-solution per trunk were added and the solution was stirred for 15 minutes with serum free medium at room temperature using a magnetic stirrer. Trypsinized cells were poured through a layer of mesh into a beaker. All cells were transferred to one 225 ml-centrifuge tube and centrifuged down at 20° C., 470xg for 7 minutes in a bench top centrifuge. After discarding the supernatant, the pellet was resuspended in 1 ml fresh pre-warmed (37° C.) serum free growth medium comprising 10 ng/ml EGF per trunk by pipetting up and down thoroughly. Fresh prewarmed (37° C.) serum free growth medium comprising 10 ng/ml EGF was added to a total volume of 150 ml. The centrifugation step was repeated. The supernatant was removed and the pellet was resuspended as described above. Fresh prewarmed (37° C.) serum free growth medium comprising 10 ng/ml EGF was added to a total volume of 100 ml. Cells were counted as described in the following section. The required amounts of cells were seeded in roller bottles with serum free growth medium comprising 10 ng/ml EGF and incubated at 37° C. Cells were ready for virus infection at day four after seeding.

Example 2

Counting Cell Density

A sample of the cell suspension (see section CEF preparation) was taken and mixed with one volume of Trypan blue, resulting in a final cell count of 20 to 100 cells per 16 small squares of a hemocytometer supplied by Fuchs-Rosenthal under the name of Hemocytometer Fast Read 102 (1:2-1:10 dilution). The sample was taken immediately after resuspending the cells in order to prevent reaggregation or sedimentation of the cells. After a few minutes of incubation time with Trypan blue in order to get the dye properly into dead cells, 10 µl of the cell suspension was added to the hemocytometer. Only white, living cells were counted under a light microscope using a 10× objective. In total, 3 representative big squares consisting of 3×16 small ones were counted. From every big square only two borders in L-Form were included in the counting. The average of counted cells was taken and the final cell concentration was calculated using the following formula: Average cell number x dilution $\times 10^4$=cells/ml. Finally the cell suspension was diluted to the desired working concentration.

Example 3

Effect of the Addition of a Factor Selected from Growth Factors and Fibronectin to a Serum Free Culture Medium on the Formation of a CEF-Monolayer In preliminary experiments it was shown that CEF cells do not attach to the surface of cell culture vessels if medium 199 is used that does not comprise FCS. Moreover, no monolayers are formed. Normal monolayer formation is observed if medium 199 containing 7% FCS is used. It was analyzed whether attachment and growth of CEF cells in serum free medium 199 can be achieved if recombinant Epidermal Growth Factor (r-hEGF) and Fibronectin (FN) are added to the medium.

For the experiments CEF cells were grown in medium 199 with the different additives alone or in combination. Cells grown in medium 199 without any additives served as negative control. Cells cultivated in medium 199 comprising 7% FCS served as positive control. All experiments were conducted in 6-well cell culture plates with 3 ml medium. The additives were treated according to the data sheets of the supplier before being used for the cell culture. Fibronectin was allowed to adsorb to the surface of the cell culture plates for 25 minutes before use. Fibronectin was used in a concentration of 3 µg/cm$^2$ and EGF was used in a concentration of 10 ng/ml. Before adding any cells the cell culture plates were brought into contact with the fibronectin-containing medium for 25 minutes.

Every culture medium plus the additives to be tested was cultured in duplicate. The 6-well cell culture plates were incubated for 4 days at 37° C. From day 1 to 4 the attachment and growth of the cells was evaluated using a microscope.

For the positive control a normal attachment and growth of the CEF cells has been observed. For Medium 199 without additives nearly no attachment of CEF cells could be observed.

A crucial improvement in the forming of a monolayer was seen by the use of EGF added to Medium 199 compared to Medium 199 without additives. It was found that the cells attached and formed the typical fibroblast morphology. Furthermore, a continuous growth could be observed over the whole period of 4 days.

An improvement of cell attachment was also achieved by adding fibronectin to the culture medium. The addition of both, EGF and Fibronectin resulted in a slight improvement compared to the addition of EGF only and Fibronectin only.

In summary, monolayer formation of CEF cells in the serum-free Medium 199 can be supported by the use of the additives EGF and Fibronectin.

Moreover, in parallel sets of experiments $1 \times 10^7$ CEF cells were seeded in medium comprising 10% FCS, medium not comprising FCS and medium not comprising FCS but comprising EGF. The cell number was counted 2 days after seeding. The number of cells amounted to 42%, 6% and 44%, respectively, of the cell number used for seeding. Thus, the results for the cells seeded in serum free medium comprising EGF were as good as the results obtained with medium comprising FCS and significantly better than with medium neither containing serum nor EGF.

In addition the medium comprising EGF was compared to various standard serum free media, such as DMEM, Opti-Mem or 293-SFM. To this end $1 \times 10^7$ CEF cells were seeded in the various serum-free media and cultivated for 4 days. The number of cells cultivated in medium comprising EGF was 24, 5 and 12 times higher than the number of cells cultivated in serum free DMEM, Opti.Mem and 293-SFM, respectively.

Example 4

Infection of CEF Cells with MVA

CEF cells were infected four days after seeding in roller bottles. At that time point cells have grown to an adequate monolayer. Cells were infected with a MOI of 1 or 0.1 MVA. For the infection the growth medium was removed from the flasks. The desired amount of virus per roller bottle was diluted in 20 ml of the appropriate infection medium without serum. At this stage the serum free medium may or may not comprise a factor selected from growth factors and fibronectin. Cells were incubated with the virus for 1 hour at 37° C. at 0.3-0.5 rpm in a roller bottle incubator. After 1 hour the roller bottles were filled with the appropriate serum free growth medium to a total volume of 200 ml per roller bottle. At this stage the serum free medium may or may not comprise a factor selected from growth factors and fibronectin. Virus replication was stopped after 48 or 72 hours by freezing the roller bottles to −20° C.

Example 5

Preparation of Viral Extracts from Infected CEF Cells and Titration of MVA

The frozen roller bottles were thawed at room temperature. During the thawing process the cells detach from the surface of the roller bottles and can mechanically be removed by shaking the flasks. Virus/cell suspension was harvested and aliquoted to smaller volumes. To release the virus from the infected cells, virus/cell suspensions were 3 times freeze/thawed. The freeze/thawed virus samples were used for titration.

Titrations were performed on $1^{st}$ passage CEF cells in 96-well plates, using 10-fold dilutions of viral suspension and 8 replicates per dilution. After the infection, infected cells were visualized with an anti-vaccinia virus antibody and an appropriate staining solution.

In detail, at day zero of the assay primary CEF cells (see section "preparation of Chicken Embryo Fibroblast (CEF) cells") were trypsinized and counted as described in the section "counting cell density". The cells were diluted to $1 \times 10^5$ cells/ml in RPMI medium with 7% FCS. Following this dilution, 100 µl were seeded in each well of the 96-well plates using a multichannel pipette. Cells were incubated over night at 37° C. and 5% $CO_2$. The virus samples to be titrated (see section "preparation of viral extracts from infected CEF cells) were serially diluted in 10-fold steps from $10^{-1}$-$10^{-12}$ using RPMI without serum. This serial dilution is carried out by adding 900 µLI RPMI to all the wells of a 96-deep-well plate. 100 µl of virus sample was added to all the wells of the first row and mixed. Thereafter, 100 µl of each sample were transferred to the next row of wells using a multi-channel pipette. The 96-deep-well plates were kept on ice when performing the dilutions. Plates were incubated for 5 days at 37° C. and 5% $CO_2$ to allow the infection to proceed. After 5 days, cells were immunohistochemically stained with a vaccinia virus specific antibody. For the staining, the culture medium was removed by turning the 96-well plate upside down over a receptacle. Cells were fixed with 100 µl/well methanol/acetone (1:1) mixture for 10 minutes at room temperature. The fixing solution was removed and plates were air-dried. After drying, cells were washed once with PBS and incubated for 1 hour at room temperature with the anti-vaccinia virus antibody (Anti-Vaccinia virus antibody, rabbit polyclonal, IgG fraction (Quartett, Berlin, Germany #9503-2057) diluted to 1:1000 in PBS with 3% FCS. After removing the antibody, cells were washed twice with PBS and incubated for 1 hour at room temperature with HRP-coupled (Horseradish Peroxidase-coupled) anti-rabbit antibody (Anti-rabbit IgG antibody, HRP-coupled goat polyclonal (Promega, Mannheim, Germany # W4011) diluted to 1:1000 in PBS with 3% FCS. Again, cells were washed with PBS and stained either with o-Dianisidine or TMB. For using the o-Dianisidine staining method, cells were incubated with 100 µl/well staining solution consisting of 5 mg o-Dianisidine and 180 µl 30% $H_2O_2$ per 60 ml of 50 mM phosphate-citrate buffer. Cells were incubated at room temperature until they stained brown. Infected cells were clearly visible after 1-3 hours. Using the TMB staining method, cells were incubated with 30 µl/well 1.2 mM TMB (Seramun Diagnostica GmbH). After 15 minutes incubation time, the TMB solution was removed and cells were washed once with PBS. Infected cells appear dark blue. The plates were scored for infected cells. The viral titer was calculated using the formula of Spearman and Kaerber. For the calculation of the $TCID_{50}$ every well showing brown or blue cells was marked positive. Because assay parameters are kept constant, the following simplified formula was used:

Virus titer$[TCID_{50}/ml] = 10^{[a+1.5+xa/8+xb/8+xc/8]}$    i.

b. a=dilution factor of last column, in which all eight wells are positive c. $x_a$=number of positive wells in column a+1
d. $x_b$=number of positive wells in column a+2
e. $x_c$=number of positive wells in column a+3

Example 6

Optimal Seeding Density for CEF Cells in Serum Free Medium and Optimal Amount of MVA for Infection of CEF Cells An optimal seeding cell density of $7.5 \times 10^7$ cells/850 $cm^2$ (surface of one roller flask) was determined for serum-free CEF growth. Cells were able to build a good monolayer without forming big clumps at day four after seeding and could be infected at this time point.

Experiments were carried out to determine the best level of viral inoculation and length of the infection for the maximum production of MVA from CEF cells cultured in a serum-free process. CEF cells were seeded at a density of $7.5 \times 10^7$ cells/850 $cm^2$ in medium according to the present invention. At day 4 after seeding, cells were infected with different amounts of MVA in the range of 0.05 to 1.0 $TCID_{50}$/cell of MVA. Best results were obtained with 0.1 $TCID_{50}$/cell of MVA.

Example 7

Optimal pH of Serum Free Medium for Culturing and Infection with MVA

MVA and other poxvirus infections are sensitive pH below 7.0. Poxviruses are not stable at acid pH and it is recommended that purified poxviruses are stored in a buffered solution above pH 7.0 to ensure stability and viral integrity upon storage as a liquid viral preparation. Experiments were carried out to determine the effect on virus yield when carrying out infection at different starting pH. Roller bottles were seeded with CEF cells in the usually way in serum free medium comprising 10 ng/ml EGF plus 4 mM L-glutamine and cultured for 4 days. Cells were infected with MVA at 0.1 $TCID_{50}$/cell in serum free medium comprising 10 ng/ml EGF plus L-glutamine and 1 mM asparagine at different pH's ranging from 6.5 to 9.0. At 72 hours post infection, the pH of the medium was measured and viral yields were determined by titrating cell extracts in the usual manner. The results are presented in the following table, which shows the effect of initial pH of the medium at the start of the infection on virus yield.

| | serum free medium comprising 10 ng/ml EGF | |
|---|---|---|
| Starting pH | pH at 72 h p.i. | Titer [$TCID_{50}$/ml] |
| 6.5 | 7.05 | $0.56 \times 10^7$ |
| 7.0 | 7.34 | $10.0 \times 10^7$ |
| 7.5 | 7.53 | $5.60 \times 10^7$ |
| 8.0 | 7.68 | $8.60 \times 10^7$ |
| 8.5 | 7.75 | $7.80 \times 10^7$ |
| 9.0 | 8.03 | $0.65 \times 10^7$ |

For the infections carried out in serum free medium comprising 10 ng/ml EGF supplemented with L-glutamine and asparagine, the viral production was relatively constant with a starting pH from 7.0 to 8.5 but viral productions were low at starting pH of 6.5 and 9.0. Best yield was obtained at starting pH 7.0. Commercially available standard serum free media usually have a pH of 7.4. Therefore adjusting the pH of the serum free medium to 7.0 can help to improve virus yield.

Example 8

Effect of Added Asparagine to the Serum Free Medium

Preliminary experiments have revealed that the amount of asparagine may be limiting during the cultivation of CEF cells and the infection of CEF cells with MVA. To overcome the depletion of asparagine in the serum free media during the culturing and infection process, extra asparagine was added to the medium as a supplement before infecting CEF cells. To determine the optimal amount of asparagine to supplement the medium with, roller bottles were seeded with CEF cells ($7.5 \times 10^7$ cels/850 cm$^2$) in serum free medium comprising 10 ng/ml EGF plus 4 mM L-glutamine. Four days after seeding cells were infected with MVA at 0.1 TCID$_{50}$/cell in serum free medium comprising 10 ng/ml EGF plus 4 mM L-glutamine supplemented with different asparagine concentrations (0.5, 1.0 and 1.5 mM). Viral replication was stopped at 72 hours post infection and viral titers were determined. The results are shown in the following table that shows the production of MVA from CEF cells supplemented with different levels of asparagine for the infection stage. The titers represent the averages of 3 roller bottles per asparagine supplementation.

| Supplement Asparagine | Viral titers after 72 hours infection [TCID$_{50}$/ml] |
|---|---|
| 0.0 mM | $1.8 \times 10^8$ |
| 0.5 mM | $1.3 \times 10^8$ |
| 1.0 mM | $6.8 \times 10^8$ |
| 1.5 mM | $1.0 \times 10^8$ |

The results demonstrate that supplementing the serum free medium comprising 10 ng/ml EGF medium with asparagine could improve viral production and that supplementation to 1 mM for the infection process was optimal.

Example 9

Re-Derivation of Viruses

It is the aim of this example to show the usefulness of the methods according to the present invention for the re-derivation of viruses. We therefore intentionally cultivate MVA-BN under standard serum containing conditions. Accordingly, such vaccine may potentially comprise undesired viral contaminants or infectious agents such as BSE. The virus obtained after cultivation under serum containing conditions is then used as starting material for the re-derivation of the virus under serum free conditions according to methods described in the present application to obtain a re-derived virus stock wherein the risk of said virus to contain a BSE particle is less than $10^{32}$.

MVA-BN virus seed stock: The starting material for a re-derived MVA-BN virus seed stock is an inoculate obtained by intentionally cultivating MVA-BN under standard serum containing conditions (10% fetal calf serum).

Primary CEF Cells: Primary CEF cells are prepared from certified SPF eggs as outlined below. Certified fertilised SPF eggs are supplied by Charles River SPAFAS. The flocks at Charles River are tested according to European Pharmacopoeia section 5.2.2 (REF 12.4). Upon arrival the package and the eggs are checked visually for damage and dirt. Damaged eggs are removed. The eggs are stored refrigerated for not longer than 12 days at +2° C. to 8° C. Before incubation the eggs are disinfected by spraying with MeI Sept and put into an egg incubator. Incubation is performed for 10 to 12 days (preferable 11 days) at 37.8° C.+/−0.8° C. and 60%+/−10% relative humidity.

Prior to cell preparation the eggs are transferred to a dedicated egg carton and extensively treated with MeI Sept by spraying. The eggs are allowed to dry under a laminar flow.

The eggs are opened and the embryos are removed. Dead embryos and embryos showing deformations are excluded.

The heads and feet of the embryos are cut off.

Trunks are homogenised mechanically by squeezing them in a plastic syringe.

Cells are incubated at room temperature with Trypsin/EDTA solution while stirring.

Homogenised cells are poured through one layer of mesh and collected.

The homogenised cells are centrifuged. The supernatant is discarded and the cell sediment is washed with a serum free medium according to the present invention.

The cells are pelleted again by centrifugation.

The supernatant is discarded and the cells are re-suspended in a serum free medium according to the present invention.

Cells are counted and immediately seeded in a serum free medium in appropriate culture vessels.

Plaque purification and final amplification of selected clone: The 5 rounds of plaque purification by limited dilution are conducted.

Seeding of Cells:

Primary CEF cells are seeded in a T175 flask ($1 \times 10^7$ cells/flask) in a serum free medium according to the present invention and incubated at 37° C.+/−2° C. for 3 to 8 days.

First passage CEF cells are seeded in 96 well plates ($1$-$2 \times 10^5$ cells/ml) using a serum free medium according to the present invention and incubated for 24 h at 37° C.+/−2° C.

Approximately 10 plates are used per round of plaque purification.

Infection of Cells:

10 fold serial virus dilutions ($10^{-1}$ to $10^{-10}$) are prepared in a serum free medium according to the present invention. 100 µl of the virus dilution/well are transferred to the 96 well plates containing CEF cells.

The plates are incubated for 5 to 6 days at 37° C.+/−2° C.

Isolation of Plaques:

Single virus plaques are visually detected under a microscope. 5 to 10 single plaques are collected per round of plaque purification.

Each plaque is harvested using a pipette tip by scrapping and transferred to a 1.5 ml tube. The volume is adjusted to 200 µl with a serum free medium according to the present invention.

The virus is released from the harvested cells by three cycles of freeze-thawing: freeze tube in liquid Nitrogen or at −80° C., thaw at room temperature, repeat procedure twice.

The virus suspension can be stored at −80° C. until further analysis. Alternatively if only one single virus plaque is detected per well, cells can be harvested by freeze-thawing the whole 96 well plate three-times.

For amplification, 100 µl of the virus suspension is transferred to cells grown in 12 well plates.

Amplification of Virus on 12 Well Plates:

First passage CEF cells are seeded in 12 well plates ($5\times10^4$ cells/cm$^2$) in 1 ml of a serum free medium according to the present invention and incubated for 24 h at 37° C.+/−2° C.

Cells show 80 to 100% confluence for infection.

100 µl of the virus suspension are added/well.

Cells are incubated for 48 to 72 h.

After 48 to 72 h the medium is removed and 300 µl of PBS per well are added. Cells are harvested in PBS and transferred to a 1.5 ml tube. If cells are already detached they are harvested (by scraping) directly in the media and transferred to a 1.5 ml tube.

The virus is released from the harvested cells by three cycles of freeze-thawing: freeze tube in liquid Nitrogen or at −80° C., thaw at room temperature, repeat procedure twice.

The virus suspension can be stored at −80° C. until further analysis.

Screening of Amplified Virus:

200 µl of the solution are used for DNA preparation and PCR screening.

The remaining 100 µl are used for the next plaque purification round.

Final amplification of selected clone: After 5 rounds of plaque purification, the final selected clone is further amplified to obtain enough material to produce a new master seed. The minimal amount of virus needed for production of a new master seed is $1\times10^8$ TCID$_{50}$ in 16-20 ml. The selected clone (already amplified on a 12 well plate) is transferred to a T25 cell culture flask for amplification. The cell virus suspension is harvested by three cycles of freeze-thawing. The virus suspension is then transferred to a T75 cell culture flask for amplification and harvested. The virus is released by 3 cycles of freeze-thawing. Final amplification is performed in 3 to 5 T175 cell culture flasks. Material from 3 to 5 T175 flasks is harvested and subjected to 3 cycles of freeze-thawing. The virus suspension is titrated, checked for sterility and tested for identity by PCR analysis of the 6 deletion sites.

Production of new master seed: Primary CEF cells are seeded in roller bottles (850 cm$^2$) with $7.5\times10^7$ CEF cells in 200 ml of a serum free medium according to the present invention. 2 to 5 roller bottles are seeded and incubated for 4 days at 37° C.+/−2° C., 0.3 rpm (0.2 rpm) in a roller incubator. A virus suspension is prepared with a final titer of $1.0\times1\times10^6$ TCID$_{50}$ (±0.5 log) in RPMI media. 10 ml are needed per roller bottle. This corresponds to an MOI of 0.1. The medium is removed from the roller bottles. 10 ml of the virus suspension is added to each roller bottle and incubated for 1-3 hrs in a roller incubator. 140 ml RPMI are added and incubated for 72 hours (±8 hours), 0.5 rpm (±0.2 rpm).

Bottles are checked macroscopically for microbial contamination. The roller bottles are transferred into a −20° C. freezer, and the cell/virus suspension is allowed to freeze. The roller bottles are stored at room temperature until the suspension has started to thaw and remove cells from the wall by shaking thoroughly. The cell/virus suspension is allowed to thaw completely. The cell/virus suspension is harvested into an appropriate vessel and aliquot a 4.5 ml in 5 ml cryotubes. Approximately 100 vials can be obtained from one roller bottle. Filled virus suspension is stored at −20° C.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

We claim:

1. A cell culture comprising chicken embryo fibroblast cells (CEFs), which have not previously been cultured in a medium containing serum, in a serum free medium, wherein the CEFs are capable of replication for at least 4 days in the serum free medium, and wherein the serum free medium comprises epidermal growth factor at a concentration of 1-50 ng/ml.

2. The cell culture of claim 1, wherein the serum free medium comprises a fibronectin.

3. The cell culture of claim 1, wherein the epidermal growth factor is human epidermal growth factor.

4. The cell culture of claim 3, wherein the epidermal growth factor is recombinant human epidermal growth factor at a concentration of 5-50 ng/ml.

5. The cell culture of claim 4, wherein the epidermal growth factor is recombinant human epidermal growth factor at a concentration of 5-20 ng/ml.

6. The cell culture of claim 1, wherein the serum free medium comprises a microbial extract, a plant extract, or an extract from a non-mammalian animal.

7. The cell culture of claim 1, wherein the serum free medium comprises asparagine in the range of 0.8-1.8 mM.

8. The cell culture of claim 1, wherein the serum free medium comprises glutamine in the range of 1-5 mM.

9. The cell culture of claim 8, wherein the serum free medium comprises glutamine in the range of 2-4 mM.

10. The cell culture of claim 1, wherein the CEFs are infected with a virus.

11. The cell culture of claim 2, wherein the epidermal growth factor is human epidermal growth factor.

12. The cell culture of claim 11, wherein the epidermal growth factor is recombinant human epidermal growth factor at a concentration of 5-50 ng/ml.

13. The cell culture of claim 12, wherein the epidermal growth factor is recombinant human epidermal growth factor at a concentration of 5-20 ng/ml.

14. The cell culture of claim 2, wherein the fibronectin is human plasma fibronectin.

15. The cell culture of claim 14, wherein the fibronectin is human plasma fibronectin at a concentration of 1-10 µg/ml.

16. The cell culture of claim 2, wherein the serum free medium comprises a microbial extract, a plant extract, or an extract from a non-mammalian animal.

17. The cell culture of claim 2, wherein the serum free medium comprises asparagine in the range of 0.8-1.8 mM.

18. The cell culture of claim 2, wherein the serum free medium comprises glutamine in the range of 1-5 mM.

19. The cell culture of claim 18, wherein the serum free medium comprises glutamine in the range of 2-4 mM.

20. The cell culture of claim 2, wherein the CEFs are infected with a virus.

* * * * *